United States Patent [19]
Nathan et al.

[11] Patent Number: 5,833,660
[45] Date of Patent: Nov. 10, 1998

[54] NON-REUSABLE SYRINGE

[76] Inventors: Elizabeth S. Nathan, 1175 Park Ave., New York, N.Y. 10128; Gabriella L. Pollack, 131-135 E. 66th St., New York, N.Y. 10021

[21] Appl. No.: 972,702
[22] Filed: Nov. 18, 1997

Related U.S. Application Data

[63] Continuation of Ser. No. 587,514, Jan. 17, 1996, abandoned.
[60] Provisional application No. 60/000,079, Jun. 8, 1995.
[51] Int. Cl.$^6$ ..................................................... A61M 5/50
[52] U.S. Cl. ........................................... 604/110; 604/221
[58] Field of Search .................................... 604/110, 187, 604/218, 220–223, 228, 276, 200, 203, 204

[56] References Cited

U.S. PATENT DOCUMENTS

| | | |
|---|---|---|
| 3,478,937 | 11/1969 | Solowey . |
| 4,233,975 | 11/1980 | Yerman .................................... 604/110 |
| 4,687,467 | 8/1987 | Cygielski ................................. 604/110 |
| 4,713,056 | 12/1987 | Butterfield . |
| 4,731,068 | 3/1988 | Hesse . |
| 4,775,363 | 10/1988 | Sandsdalen . |
| 4,775,364 | 10/1988 | Alles . |
| 4,790,822 | 12/1988 | Haining ................................... 604/110 |
| 4,826,483 | 5/1989 | Molnar, IV . |
| 4,850,968 | 7/1989 | Romano . |
| 4,878,899 | 11/1989 | Plouff . |
| 4,923,443 | 5/1990 | Greenwood et al. . |
| 4,950,240 | 8/1990 | Greenwood et al. . |

(List continued on next page.)

OTHER PUBLICATIONS

News Release: "One–Use 'Self–Destructing' Hypodermic Syringe Invented By Orange County Doctor And Engineer" (Oct. 19, 1988).

Becton Dickinson & Co. 1994 Annual Report, p. 19 on B–D® SOLOSHOT syringe.
Becton Dickinson & Co. brochure (copyright 1995) on B–D® Safety–Lok syringe.
Becton Dickinson & Co. brochure (copyright 1994) on B–D® MedSaver syringe.
Univec Inc., Garden City, New York 11530 package (undated) containing Single Use Locking Syringe, sent to applicants by Univec on May 10, 1995.
"First International Conference On Self–Destructing (Non–Reusable) Syringes," Apr. 18–19, 1991 (published by NYU Medical Center).
"Self–Destructing (Non–Reusable) Syringes," *The Lancet*, vol. 338, pp. 438–439 (Aug. 17, 1991).

*Primary Examiner*—Ronald Stright, Jr.
*Assistant Examiner*—A. T. Nguyen
*Attorney, Agent, or Firm*—John E. Nathan

[57] ABSTRACT

Non-reusable syringe having a syringe body, a hypodermic needle and a slidable piston for drawing and discharging fluid through the needle. In one embodiment, the non-reusable syringe includes a movable engagement member. A first position of the movable engagement member permits initial withdrawal of the piston, allowing fluid to be drawn into the syringe. Initial withdrawal of the piston moves the movable engagement member into a second position. After the fluid has been substantially discharged, the second position of the movable engagement member captures the piston and prevents the piston from being withdrawn again. In another embodiment, the movable engagement member is mounted on, and movable with respect to, the piston. The non-reusable syringe can also include a releasable connection between the piston and the piston driver. Once the piston has been captured, a second attempt to use the syringe will separate the piston from the piston driver, further preventing reuse of the syringe. The non-reusable syringe can also include a stop mechanism to prevent complete withdrawal of the piston, thereby precluding the possibility of tampering with or removing the movable engagement member and/or the piston.

12 Claims, 4 Drawing Sheets

U.S. PATENT DOCUMENTS

| | | | |
|---|---|---|---|
| 4,973,309 | 11/1990 | Sultan . | |
| 4,978,339 | 12/1990 | Labouze et al. . | |
| 4,986,812 | 1/1991 | Perler . | |
| 4,986,813 | 1/1991 | Blake, III et al. . | |
| 5,000,735 | 3/1991 | Whelan | 604/110 |
| 5,000,737 | 3/1991 | Free et al. . | |
| 5,045,063 | 9/1991 | Spielberg | 604/110 |
| 5,062,833 | 11/1991 | Perler . | |
| 5,078,686 | 1/1992 | Bates . | |
| 5,085,638 | 2/1992 | Farbstein et al. . | |
| 5,088,987 | 2/1992 | Noonan, Jr. . | |
| 5,106,372 | 4/1992 | Ranford | 604/110 |
| 5,135,495 | 8/1992 | Arcusin . | |
| 5,149,323 | 9/1992 | Colonna . | |
| 5,181,912 | 1/1993 | Hammett . | |
| 5,195,975 | 3/1993 | Castagna . | |
| 5,201,709 | 4/1993 | Capra et al. . | |
| 5,215,524 | 6/1993 | Vallelunga et al. . | |
| 5,226,881 | 7/1993 | Pickhard | 604/110 |
| 5,226,882 | 7/1993 | Bates . | |
| 5,290,235 | 3/1994 | Polyblank et al. . | |
| 5,328,484 | 7/1994 | Somers et al. . | |
| 5,389,075 | 2/1995 | Vladimirsky . | |
| 5,415,646 | 5/1995 | Roth . | |
| 5,453,092 | 9/1995 | Merriman . | |
| 5,536,253 | 7/1996 | Haber et al. | 604/110 |

NON-REUSABLE SYRINGE

CROSS REFERENCE TO RELATED APPLICATIONS

This is a continuation of application Ser. No. 08/587,514 filed Jan. 17, 1996 (now abandoned), entitled Non-Reusable Syringe, which claims the benefit of United States provisional application No. 60/000,079, filed Jun. 8, 1995.

This claims the benefit of United States provisional application No. 60/000,079, filed Jun. 8, 1995.

BACKGROUND OF THE INVENTION

This invention relates to hypodermic syringes capable of being used only once.

It is well-known that Acquired Immunodeficiency Syndrome (AIDS) is a destructive and deadly disease for which a cure has not been found, and that Human Immunodeficiency Virus (HIV)—the virus that causes AIDS—is transmitted by the exchange of body fluids such as blood. Despite these established medical facts, many injecting drug users continue to share and thus reuse hypodermic syringes contaminated with HIV-infected blood. This practice is now a leading cause of HIV infection and, ultimately, AIDS.

To address this epidemic, various attempts have been made to design hypodermic syringes that are capable of being used only once, in order to eliminate the possibility of sharing a hypodermic syringe contaminated with HIV-infected blood. Illustrative is Somers et al. U.S. Pat. No. 5,328,484.

As the AIDS epidemic has grown, so has the need for a non-reusable syringe that can be readily and inexpensively manufactured, that is reliable in operation, that permits the operator to remove air bubbles from the syringe using the same techniques employed with conventional syringes, and that does not require the operator to perform any special or additional steps not required by conventional syringes.

Accordingly, it is an object of the invention to provide a non-reusable syringe employing a small number of parts, and which can be mass-produced using conventional materials used in hypodermic syringes.

It is a further object of the invention to provide a non-reusable syringe capable of reliably drawing and dispensing fluids from and into the body.

It is a further object of the invention to provide a non-reusable syringe that operates in the same manner as a conventional syringe, including the removal of air bubbles from the syringe before fluid is dispensed into the body.

It is a further object of the invention to provide a non-reusable syringe that does not require the use of special or additional steps not employed during the operation of a conventional syringe.

SUMMARY OF THE INVENTION

These and other objects of the invention are accomplished, in accordance with the principles of the invention, by providing a hypodermic syringe with a movable engagement member. In one embodiment of the invention, before the syringe is used, the movable engagement member is in a first position that permits withdrawal of the syringe piston in the conventional manner, thus allowing fluid to be drawn into the syringe. During initial withdrawal of the piston, the movable engagement member is moved to a second position. After the syringe is filled to capacity with the fluid to be dispensed, conventional techniques can be used to remove any air bubbles from the syringe (e.g., by holding the syringe vertically with the needle pointing up and then moving the piston back and forth and/or gently striking the side of the syringe). The syringe is then "fired" by moving the piston toward the needle, thus discharging the fluid in the conventional manner. When the fluid is substantially discharged, the movable engagement member engages and captures the piston, thereby preventing reuse of the syringe.

In another embodiment of the invention, the movable engagement member is mounted on, and movable with respect to, the piston. In its first position, the movable engagement member permits initial withdrawal of the piston, and is movable by the initial withdrawal to a second position which engages the syringe body following substantial discharge of the fluid, thereby preventing further use of the syringe.

The non-reusable syringe constructed according to the invention can include a releasable connection between the piston and the piston driver. Once the piston has been captured, a second attempt to use the syringe will separate the piston from the piston driver, further preventing reuse of the syringe. The non-reusable syringe can also include a stop mechanism to prevent complete withdrawal of the piston, thereby precluding the possibility of tampering with or removing the movable engagement member and/or the piston.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
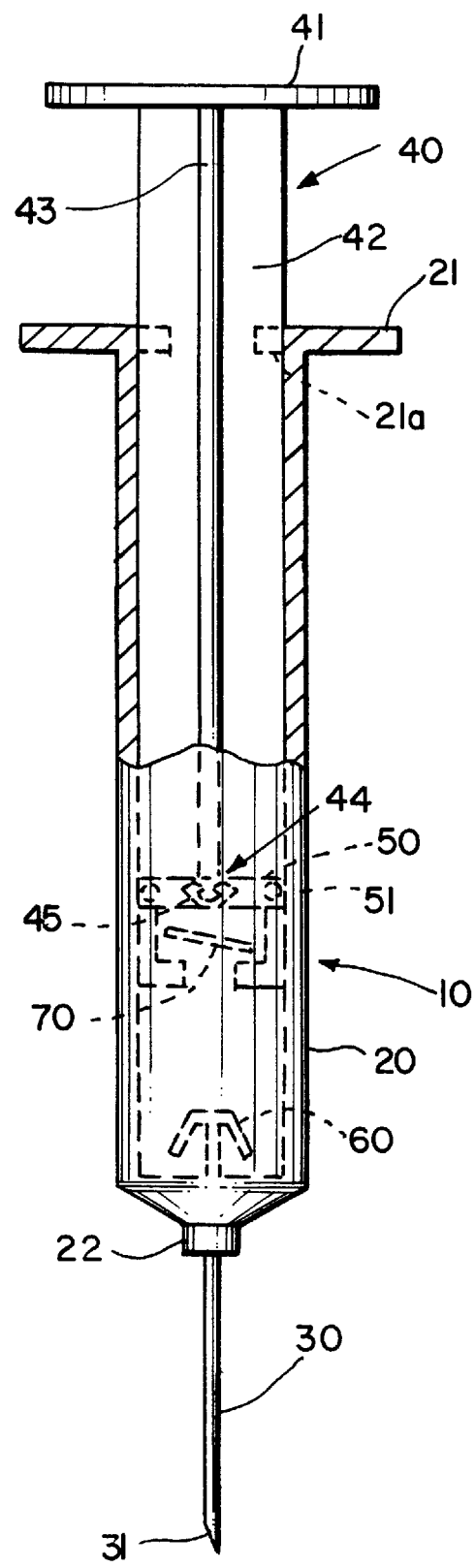
FIG. 1 is a partial sectional view of one embodiment of the non-reusable syringe constructed according to the present invention, with the piston driver shown partially withdrawn for clarity.

FIG. 1 depicts, in partial section, an overall view of one embodiment of the non-reusable syringe 10 constructed according to the present invention. The non-reusable syringe 10 contains a syringe body 20, preferably of circular cross section. Syringe body 20 is typically made of plastic material and can be fabricated by methods well known to those skilled in the syringe manufacturing art, such as injection molding. Syringe body 20 has an integrally molded flange 21 at one end, which is held in the conventional manner between the index and middle fingers when the syringe is to be discharged. Flange 21 may also be fabricated separately from syringe body 20 and attached thereto with an adhesive or other suitable fastening means. Attached to or integrally molded with the other end of syringe body 20 is a fitting 22 adapted to receive and retain a hypodermic needle 30 having a sharpened tip 31 for puncturing the skin. Needle 30 may be enclosed with a conventional protective sheath (not shown), which is removed before the syringe is used and may be replaced after use as an additional safety precaution.

Slidably received in syringe body 20 is a piston driver 40, which can also be made by conventional plastic injection molding. Attached to or preferably integrally molded onto one end of piston driver 40 is a flange 41, which is held in the conventional manner to fill and discharge syringe 10. Piston driver 40 includes longitudinal ribs 42 and 43, preferably integrally molded thereon and annularly displaced from one another by 90°, which support piston driver 40 in syringe body 20. Piston driver 40 includes, at the end opposite flange 41, a connector 44 which is preferably integrally molded with piston driver 40. Connector 44 seats in an insert 45 recessed into the top portion of a piston 50. Insert 45 is made of rubber or a synthetic elastomer, thus forming a releasable connection between connector 44 and insert 45. The releasable connection is made sufficiently strong to maintain the connection between connector 44 and insert 45 when piston 50 is initially withdrawn, as hereinafter described. Connector 44, and the associated seat in insert 45, may be of any other suitable shape in addition to that shown in FIGS. 1, 2, 4 and 5, such as a sphere which thus forms a releasable ball and socket joint.

As an additional safety precaution, a conventional cap or sheath (not shown) can be placed over flanges 21 and 41 to prevent inadvertent withdrawal of piston driver 40 before syringe 10 is to be used, such as during transit or handling.

Piston 50, described in detail with reference to FIGS. 2–5, is preferably made of a substantially rigid material and can also be injection molded plastic. An O-ring 51 made of rubber or a synthetic elastomer is fitted in the outside surface of piston 50, thus forming a fluid seal with the inside of syringe body 20.

A movable engagement member 60 is integrally molded with syringe body 20 at its end adjacent needle 30. Alternatively, movable engagement member 60 may be a separate mechanism, and attached to the inside of syringe body 20 at the end adjacent to needle 30 with an adhesive or other suitable fastening means. The construction and operation of movable engagement member 60 are described in detail with reference to FIGS. 2–5.

A retaining member 70 controls the position of movable engagement member 60, also as hereinafter described with reference to FIGS. 2–5.

Figure 2:
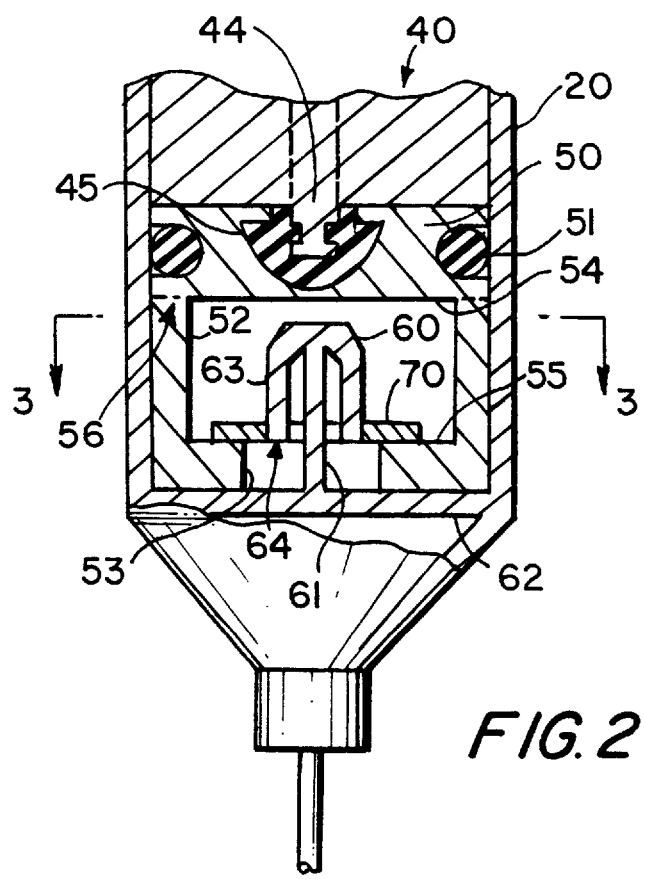
FIG. 2 is an enlarged partial sectional view of the non-reusable syringe shown in FIG. 1, showing the movable engagement member before the syringe is used.
Figure 3:
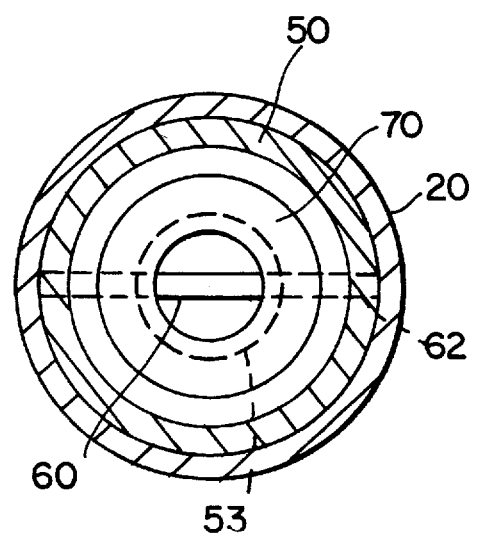
FIG. 3 is a sectional view of the non-reusable syringe shown in FIG. 2, taken along the line 3—3.

Referring to FIGS. 2–3, piston 50 is preferably made of a substantially rigid material such as injection molded plastic. O-ring 51 forms a liquid seal between piston 50 and syringe body 20. Piston 50 has a cavity defined by the annular walls 52 and 53, the top surface 54 and the ledge surface 55. Annular wall 53 further defines an opening to the cavity, which is dimensioned to permit piston 50 to be initially withdrawn when movable engagement member 60 is held by retaining member 70. Retaining member 70 is dimensioned so that it engages ledge surface 55 when piston 50 is initially withdrawn.

Piston 50 may be made in two parts, for example along the dotted line 56 shown in FIG. 2, to facilitate placement of retaining member 70 during the manufacturing process. After retaining member 70 is in place, the top portion of piston 50 may be joined to the bottom portion by an adhesive, thermal fusing, etc.

Movable engagement member 60 is preferably spring-like and formed from a material capable of deformation yet able to return to its original shape. Various materials are suitable for this purpose, for example a plastic such as polypropylene, or a metal compatible with medical applications such as stainless steel. Movable engagement member 60 is supported by a post 61 and a cross bar 62. Preferably, movable engagement member 60, post 61 and cross bar 62 are plastic and are all integrally molded with syringe body 20, as shown in FIGS. 1–2. Movable engagement member 60 includes two legs 63, which are normally outwardly extending as shown generally in FIG. 1. The length of legs 63 are dimensioned so that following use of syringe 10, when legs 63 are in their normal outwardly extending position, the ends 64 of legs 63 will interfere with ledge 55, thus preventing reuse of syringe 10.

Other variations of movable engagement member 60 are possible, such as a spring-loaded mechanism capable of moving from a first position that permits initial withdrawal of piston 50, to a second position that captures piston 50 following substantial discharge of the fluid from syringe 10.

Retaining member 70 is preferably of circular shape, but may be any other suitable configuration. Retaining member 70 may be made of plastic, a metal such as stainless steel, or any other substantially rigid material suitable for medical applications. As shown in FIGS. 2–3, legs 63 are deformed and held in that position by retaining member 70 until syringe 10 is to be used. Because retaining member 70 is dimensioned to engage ledge surface 55, initial withdrawal of piston 50 will remove retaining member 70 from movable engagement member 60, thus freeing legs 63 to return to their normal outwardly extending position.

Retaining member 70 is made sufficiently thick so that it seats on ledge 55 while still retaining legs 63 in their deformed position. This will prevent retaining member 70 from slipping off ends 64 before syringe 10 is to be used, such as might occur during transit or handling. Alternatively, to insure that retaining member 70 does not slip off ends 64, optional protrusions 65 (shown with dotted lines in FIG. 4) may be provided adjacent ends 64.

Other methods to hold legs 63 in their deformed position can be employed, such as the use of frangible connections between legs 63 and post 61, spring-loaded members, snap rings and the like.

Figure 4:
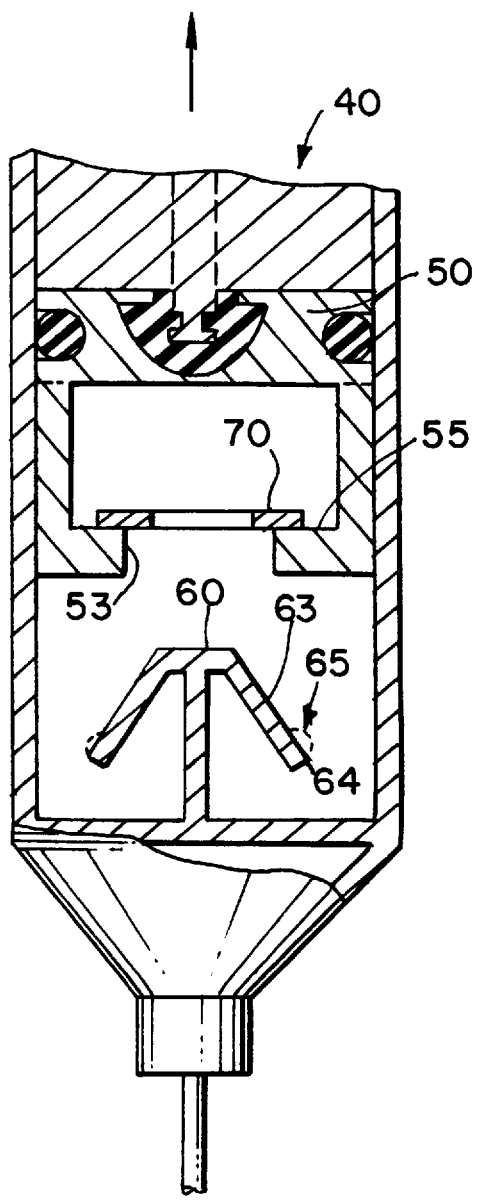
FIG. 4 is an enlarged partial sectional view of the non-reusable syringe shown in FIG. 1, during initial withdrawal of the piston as fluid is drawn into the syringe body.
Figure 5:
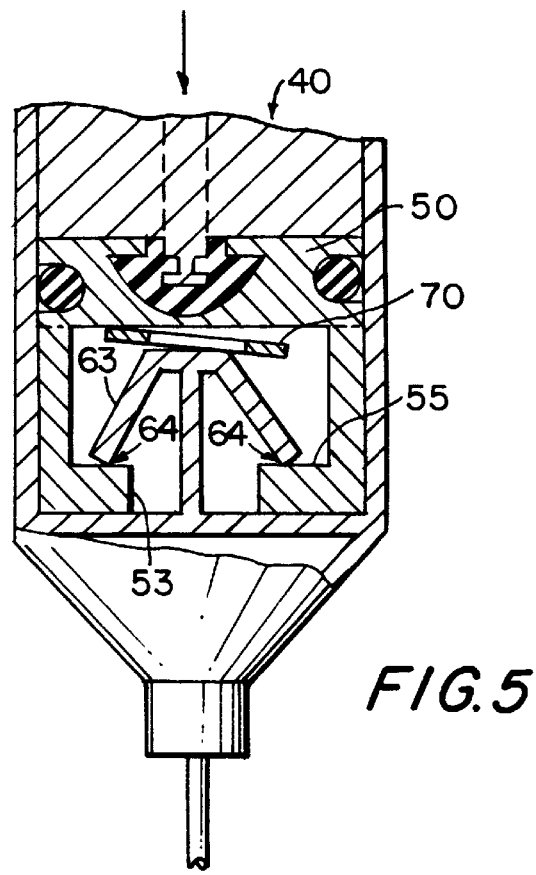
FIG. 5 is an enlarged partial sectional view of the non-reusable syringe shown in FIG. 1, after the fluid has been discharged and the piston captured, thus preventing reuse of the syringe.

The operation of syringe 10 is shown in FIGS. 4–5. Grasped in the conventional manner, piston driver 40 is withdrawn, thereby withdrawing piston 50. This causes ledge surface 55 to engage retaining member 70, which slides off legs 63. At the same time, wall 53 engages legs 63 to insure that they are held in their deformed position until movable engagement member 60 passes through the piston cavity opening. When piston 50 is withdrawn clear of movable engagement member 60, legs 63 return to their normal outwardly extending position (as shown in FIG. 4).

Further withdrawal of piston 50 permits syringe 10 to be filled to capacity in the conventional manner. Any air bubbles may then be removed using conventional methods, such as holding syringe 10 vertically with needle 30 pointing up and then moving piston driver 40 back and forth and/or gently striking the side of syringe body 20 while it is held in that position.

Syringe 10 is then "fired" by moving piston driver 40 toward needle 30, thus discharging the fluid in the conventional manner. As piston 50 approaches the bottom of syringe body 20, wall 53 engages legs 63, deforming them sufficiently to permit movable engagement member 60 to pass back through the cavity opening of piston 50. Because retaining member 70 is free to "float" within the cavity of piston 50, retaining member 70 will not reengage and deform legs 63 of movable engagement member 60. Legs 63 are then freed to return to their normal outwardly extending position (as shown in FIG. 5). Any further attempt to withdraw piston 50 will cause ends 64 of legs 63 to interfere with ledge surface 55, preventing reuse of syringe 10. Additionally, because piston 50 is now trapped at the bottom of syringe body 20, any such further effort to withdraw piston 50 will separate connector 44 from insert 45, thus disengaging piston driver 40 from piston 50.

To prevent syringe users from tampering with piston 50 and/or movable engagement member 60, or replacing piston 50 with a conventional syringe piston, a stop mechanism may be incorporated into syringe 10 to preclude complete withdrawal of piston 50, thus preventing access to both piston 50 and movable engagement member 60. The stop mechanism may take many forms, such as interfering protrusions on syringe body 20 and piston driver 40. As another example, flange 21 may be fabricated separately from syringe body 20, with an internal diameter of portion 21a less than the diameter of piston 50 and with appropriate clearance slots for longitudinal ribs 42 and 43. When attached to syringe body 20, flange 21 will prevent piston 50 from being completely withdrawn from syringe body 20.

Figure 6:
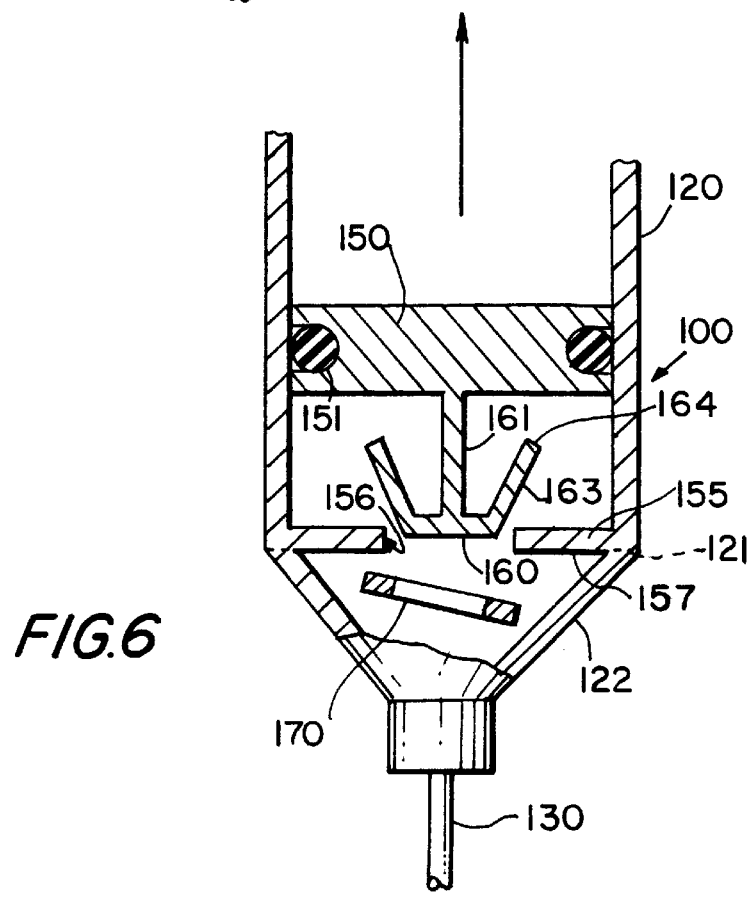
FIG. 6 is an enlarged partial sectional view of another embodiment of the non-reusable syringe constructed according to the present invention, during initial withdrawal of the piston as fluid is drawn into the syringe body. The piston driver and the releasable connection between the piston driver and the piston are removed for clarity.

FIG. 6 shows an enlarged partial sectional view of a second embodiment of the non-reusable syringe constructed according to the present invention. As will be apparent, the construction of, and the materials used in, this second embodiment are similar to the first embodiment shown in FIGS. 1–5. Accordingly, only the differences between the two embodiments will be specifically described.

Referring to FIG. 6, non-reusable syringe 100 contains syringe body 120, piston 150, needle 130, O-ring 151 and the other components of hypodermic syringes as described in detail with reference to FIG. 1. The piston driver and the releasable connection between the piston driver and piston 150 have been omitted from FIG. 6 for clarity.

Movable engagement member 160 is attached to or integrally molded with piston 150. As described with reference to FIGS. 1–5, movable engagement member 160 is deformable and includes two legs 163 with ends 164. In this second embodiment, legs 163 point away from needle 130.

A retaining member 170, preferably of circular shape, controls the position of movable engagement member 160 as in the first embodiment.

Annular ring 155 is preferably integrally molded with syringe body 120. Before initial withdrawal of piston 150, retaining member 170 holds movable engagement member 160 in the deformed position below annular ring 155. The opening of annular ring 155, defined by annular wall 156, is dimensioned to permit deformed movable engagement member 160 to be initially withdrawn. Retaining member 170 is dimensioned to have a larger diameter than the opening of annular ring 155, to prevent retaining member 170 from passing through the opening of annular ring 155.

Syringe body 120 may be made in two parts, such as along dotted line 121 shown in FIG. 6, to facilitate placement of retaining member 170 during manufacture. For example, the bottom portion 122 of syringe body 120 may be assembled first with needle 130. Retaining member 170 may be placed in position to deform movable engagement member 160, after which the top portion of syringe body 120 may be joined to bottom portion 122 by an adhesive, thermal fusing, etc.

As shown in FIG. 6, during initial withdrawal of piston 150, annular ring 155 engages retaining member 170, which slides off legs 163. When movable engagement member 160 has passed through the opening of annular ring 155, legs 163 return to their normal outwardly extending position. Further withdrawal of piston 150 and air bubble removal are now possible, as described with reference to FIGS. 2–5.

When syringe 100 is "fired" in the conventional manner, piston 150 approaches annular ring 155. Annular wall 156 sufficiently deforms legs 163 to permit movable engagement member 160 to pass through the opening of annular ring 155. Retaining member 170 "floats" between the bottom of syringe body 120 and annular ring 155, and thus will not reengage and deform legs 163 of movable engagement member 160. Legs 163 thus return to their normal outwardly extending position once they are completely through the opening of annular ring 155. Any further attempt to withdraw piston 150 will cause ends 164 of legs 163 to interfere with the surface 157 of annular ring 155, preventing reuse of syringe 100. Similarly, such an attempt to withdraw piston 150 will separate the piston driver (not shown) from piston 150, as described with reference to FIGS. 1–5.

A stop mechanism, such as described with reference to the first embodiment, may be incorporated into this second embodiment shown in FIG. 6, to prevent tampering with movable engagement member 160 or replacing the movable engagement member 160/piston 150 assembly with a conventional syringe piston.

It will be understood that the foregoing is only illustrative of the principles of this invention, and that various other modifications can be made by those skilled in the art without departing from the scope and spirit of the invention. For example, the piston may be constructed with a cavity, and the movable engagement member may be mounted on the piston within that cavity. This will reduce the combined space occupied by the piston and the movable engagement member, thus minimizing the overall size of the non-reusable syringe while maximizing the amount of fluid that may be discharged from it.

The invention claimed is:

1. A non-reusable syringe comprising:
   a syringe body having a closed end through which a hypodermic needle is mounted;
   a piston slidably received in and forming a seal with said syringe body for drawing and discharging fluid through said needle; and
   movable engagement means attached to said syringe body and having a first position not engaging said piston such that said piston can be initially withdrawn and movable by said initial withdrawal to a second position which engages said piston following substantial discharge of the fluid, thereby preventing further use of said syringe.

2. The non-reusable syringe defined in claim 1 further comprising:
   a retaining member, wherein said movable engagement means is held in said first position by said retaining member, said retaining member being disengaged from said movable engagement means by said initial withdrawal of said piston.

3. The non-reusable syringe defined in claim 1 wherein said movable engagement means is integrally molded with said syringe body.

4. The non-reusable syringe defined in claim 1 wherein said piston includes a cavity open to and facing said closed end of said syringe body and said movable engagement means in said second position engages at least one surface defining said cavity following substantial discharge of said fluid.

5. The non-reusable syringe defined in claim 1 further comprising:
   stop means on said syringe body to prevent complete withdrawal of said piston from said syringe body.

6. The non-reusable syringe defined in claim 1 further comprising:
   a piston driver releasably connected to said piston, whereby following said engagement of said piston a further attempt to use said syringe will separate said piston driver from said piston.

7. A non-reusable syringe comprising:
   a syringe body having a closed end through which a hypodermic needle is mounted;
   a piston slidably received in and forming a seal with said syringe body for drawing and discharging fluid through said needle; and
   movable engagement means attached to said piston and having a first position with respect to said piston not engaging said syringe body such that said piston can be initially withdrawn and movable by said initial withdrawal to a second position with respect to said piston which engages said syringe body following substantial discharge of the fluid, thereby preventing further use of said syringe.

8. The non-reusable syringe defined in claim 7 further comprising:
   a retaining member, wherein said movable engagement means is held in said first position by said retaining member, said retaining member being disengaged from said movable engagement means by said initial withdrawal of said piston.

9. The non-reusable syringe defined in claim 7 wherein said movable engagement means is integrally molded with said piston.

10. The non-reusable syringe defined in claim 7 further comprising:
    stop means on said syringe body to prevent complete withdrawal of said piston from said syringe body.

11. The non-reusable syringe defined in claim 7 further comprising:
    a piston driver releasably connected to said piston, whereby following said engagement of said syringe body a further attempt to use said syringe will separate said piston driver from said piston.

12. The non-reusable syringe defined in claim 7 wherein said piston includes a cavity and at least a portion of said movable engagement means in said first position is contained in said cavity.

* * * * *